United States Patent
Santhanam et al.

(10) Patent No.: US 9,445,981 B2
(45) Date of Patent: Sep. 20, 2016

(54) PLOD-2 STIMULATORS AND THEIR USE IN THE TREATMENT OF SKIN

(71) Applicant: Avon Products, Inc., Suffern, NY (US)

(72) Inventors: Uma Santhanam, Tenafly, NJ (US); Permanan Raaj Khusial, Highland Mills, NY (US)

(73) Assignee: Avon Products, Inc, New York, NY (US)

(*) Notice: Subject to any disclaimer, the term of this patent is extended or adjusted under 35 U.S.C. 154(b) by 0 days.

(21) Appl. No.: 13/721,758

(22) Filed: Dec. 20, 2012

(65) Prior Publication Data

US 2014/0179643 A1  Jun. 26, 2014

(51) Int. Cl.
| | | |
|---|---|---|
| A61K 8/44 | (2006.01) | |
| A61K 8/42 | (2006.01) | |
| A61Q 19/00 | (2006.01) | |
| A61Q 19/08 | (2006.01) | |
| A61K 8/67 | (2006.01) | |

(52) U.S. Cl.
CPC .............. *A61K 8/671* (2013.01); *A61K 8/42* (2013.01); *A61Q 19/00* (2013.01); *A61Q 19/08* (2013.01)

(58) Field of Classification Search
None
See application file for complete search history.

(56) References Cited

U.S. PATENT DOCUMENTS

| | | | |
|---|---|---|---|
| 5,767,158 A | | 6/1998 | Suetsugu et al. |
| 5,914,116 A | * | 6/1999 | Suares et al. .................. 424/401 |
| 6,159,485 A | * | 12/2000 | Yu et al. ........................ 424/401 |
| RE41,278 E | | 4/2010 | Yu et al. |
| RE41,339 E | | 5/2010 | Yu et al. |
| 9,168,283 B2 | * | 10/2015 | Zheng .................. A61K 36/889 |
| 2002/0086039 A1 | * | 7/2002 | Lee et al. ....................... 424/401 |
| 2002/0122787 A1 | * | 9/2002 | Newell et al. ............... 424/78.37 |
| 2008/0207774 A1 | * | 8/2008 | Krishnan ..................... 514/772.6 |
| 2009/0238877 A1 | * | 9/2009 | Suda et al. .................... 424/489 |
| 2010/0055138 A1 | * | 3/2010 | Margulies et al. ........... 424/401 |
| 2012/0165373 A1 | | 6/2012 | Khusial et al. |

FOREIGN PATENT DOCUMENTS

| | | | | |
|---|---|---|---|---|
| EP | 0 630 286 | * | 7/1999 | ............... B01J 13/00 |
| EP | 2 080 504 | * | 7/2009 | ............... A61K 8/44 |
| WO | 93/04669 A1 | | 3/1993 | |

OTHER PUBLICATIONS

Van Der SLOTt, A.J., A.-M. Zuurmond, A.F.J. Bardoel, C. Wijmenga, H.E.H. Pruijs, D.O. Sillence, J. Brinckmann, D. J. Abraham, C.M. Black, N. Verzijl, J. DeGroot, R. Hanemaaijer, J.M. TeKoppele, T.W.J. Huizinga, and R.A. Bank. 2003. Identification of PLOD2 as Telopeptide Lysyl Hydroxylase, an Important Enzyme in Fibrosis. Journal of Biological Chemistry. 278:40967-40972.

Walker, L.C., M.A. Overstreet, and H.N. Yeowell. 2005. Tissue-specific expression and regulation of the alternatively-spliced forms of lysyl hydroxylase 2 (LH2) in human kidney cells and skin fibroblasts. Matrix Biology. 23:515-523.

Wu, J., D.P. Reinhardt, C. Batmunkh, W. Lindenmaier, R.K.-K. Far, H. Notbohm, N. Hunzelmann, and J. Brinckmann. 2006. Functional diversity of lysyl hydroxylase 2 in collagen synthesis of human dermal fibroblasts. Experimental Cell Research. 312:3485-3494.

Hyry et al. 2009. Missense Mutations that cause bruck syndrome affect enzymatic activity,folding and oligomerization of lysyl hydrozylase 2. Journal of Biological Chemistry, 284:30917-30924.

Koss et al. 1965. Wound healing an collagen formation. The Journal of Cell Biology. 27:83-106.

Olsen et al. 1974. Ferritin-conjugated antibodies used for labeling of organelles involved in the cellular synthesis and transport of procollagen. Proc Natl Acad Sci USA. 71:2033-2037.

Harwood et al. 1975. Studies on the glycosylation of hydroxylysine residues during collagen biosynthesis and the subcellular localization of collagen galactosyltransferase and collagen glucosyltransferase in tendon and cartilage cells. Biochem J. 152:291-302.

Ruotsalainen et al. 2001. Complete genomic structure of mouse lysyl hydroxylase 2 and lysyl hydroxylase 3/collagen glucosyltransferase. Matrix Biology. 20:137-146.

Uitto et al. 1974. Hydroxylation of peptide-bound proline and lysine before and after chain completion of the polypeptide chains of procollagen. Arch Biochem Biophys. 164:210-217.

"Does Avon ANEW Clinical Pro Line Eraser Really Work?" General Medicine Community Blog Posts, Retreived from <<http://www.wellsphere.com/general-medicine-article/does-avon-anew-clinical-pro-line-eraser-really-work/1750035>>. Posted Sep. 25, 2012. pp. 1-3.

U.S. Appl. No. 13/721,687, filed Dec. 20, 2012, Santhanam et al.
U.S. Appl. No. 13/721,491, filed Dec. 20, 2012, Santhanam et al.
U.S. Appl. No. 14/521,972, filed Oct. 23, 2014, Santhanam et al.
U.S. Appl. No. 13/721,509, filed Dec. 20, 2012, Santhanam et al.

Gilkes, Daniele M. et al.,; "Hypoxia-inducible Factor 1 (HIF-1) Promotes Extracellular Matrix Remodeling under Hypoxic Conditions by Inducing P4HA1, P4HA2, and PLOD2 Expression in Fibroblasts*;" The Journal of Biological Chemistry; vol. 288; No. 15; pp. 10819-10829 (2013).

Database GNPD Mintel; Oct. 2010, "Line Eraser Treatment with A-F 33" XP002756545, Database accession No. 1883827.

* cited by examiner

*Primary Examiner* — Theodore R West

(74) *Attorney, Agent, or Firm* — Jonathan Ball

(57) ABSTRACT

Methods for preventing, ameliorating, or reducing dermatological signs of aging are provided which employ a composition comprising an effective amount of N-Acetyl-Tyrosinamide and an effective amount of a retinoid, in a cosmetically acceptable vehicle, for topical application to the skin for a time sufficient to improve the appearance of said skin.

5 Claims, No Drawings

9,445,981 B2

```
                          SEQUENCE LISTING

<160> NUMBER OF SEQ ID NOS: 4

<210> SEQ ID NO 1
<211> LENGTH: 19
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 1
acaucaugau agccguaua                                                    19

<210> SEQ ID NO 2
<211> LENGTH: 19
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 2
aaaucuaagu caagcggaa                                                    19

<210> SEQ ID NO 3
<211> LENGTH: 19
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 3
acacaaccga ggagcguau                                                    19

<210> SEQ ID NO 4
<211> LENGTH: 19
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 4
cggagaagcc cucgagcau                                                    19
```

PLOD-2 STIMULATORS AND THEIR USE IN THE TREATMENT OF SKIN

The instant application contains a Sequence Listing which has been submitted in ASCII format via EFS-Web and is hereby incorporated by reference in its entirety. Said ASCII copy, created on Dec. 20, 2012, is named SC142UUS.txt and is 1,186 bytes in size.

FIELD OF INVENTION

The present invention relates generally to compositions and methods for improving the aesthetic appearance and health of human skin. In particular, the invention relates to cosmetic compositions that include N-Acetyl-Tyrosinamide in combination with a retinoid.

BACKGROUND

Collagen is the body's major structural protein. It is composed of three protein chains wound together in a tight triple helix to form fibrils. The fibrils are cross-linked in the extracellular matrix to provide the structural scaffolding surrounding cells that helps to support cell shape and differentiation. The mesh-like collagen network binds cells together and provides the supportive framework or environment in which cells develop and function. The stimulation of collagen gives the skin its strength, durability, and smooth, plump appearance.

N-Acetyl-Tyrosinamide is an amino acid derivative with potent anti-aging and cosmetic benefits, as described in U.S. Pat. No. RE 41,278 and U.S. Pat. No. RE 41,339, the disclosures of which are hereby incorporated by reference. The present inventors have investigated the mode of operation of N-Acetyl-Tyrosinamide and discovered that it is a potent stimulator of the enzyme PLOD-2 (procollagen-lysine, 2-oxoglutarate 5-dioxygenase 2 (lysine hydroxylase-2), a homodimeric enzyme that is critical in the collagen maturation process.

Collagen synthesis and maturation is a complex multistep process. The PLOD-2 enzyme plays a fundamental role in the collagen maturation process; it catalyzes the hydroxylation of lysine residues in the nascent procollagen protein strands. The resultant hydroxylysyl groups aid in the formation of the triple helix and serve as attachment sites for cross linking in the extracellular matrix. See, Van der Slot et al., 2003, *J. Biol. Chem.*, 278:40967-40972; Walker et al., 2005, *Matrix Biology*, 23:515-523; Wu et al., 2006, *Exp. Cell Res.*, 312:3485-3494. Thus, this modification is critical for the stability of procollagen, the intermolecular cross linking of collagen fibrils and ultimately the maintenance of the dermal matrix.

The foregoing discussion is presented solely to provide a better understanding of the nature of the problems confronting the art and should not be construed in any way as an admission as to prior art.

SUMMARY OF THE INVENTION

In accordance with the foregoing objectives and others, the present invention provides cosmetic compositions and methods for improving one or more signs of dermatological aging. Without being bound by any theory, it is believed that the compositions lead to increased collagen production in the skin.

In one aspect of the invention, cosmetic compositions are provided for improving the aesthetic appearance of human skin comprising an effective amount of N-Acetyl-Tyrosinamide and an effective amount of a retinoid. Typically, N-Acetyl-Tyrosinamide and a retinoid will be formulated in a cosmetically acceptable vehicle and topically applied to a human integument, such as the skin of the face, neck, lips, hands, chest, legs, etc., for a time sufficient to enhance the health or aesthetic appearance thereof, including, for example, reducing the number or severity of wrinkles and/or fine lines. In another aspect of the invention, a method is provided for improving the aesthetic appearance of human skin comprising topically applying to an area of the skin in need thereof (e.g., wrinkled skin) an effective amount of N-Acetyl-Tyrosinamide and an effective amount of a retinoid, for a time sufficient to improve the aesthetic appearance of said human skin. In a related aspect of the invention, a method is provided of treating wrinkles and/or fines lines comprising topically applying to an area of skin in need thereof an effective amount (e.g., 0.001%-5% by weight, w/w) of N-Acetyl-Tyrosinamide and effective amount (e.g., 0.001%-5% by weight, w/w) of a retinoid (e.g., retinol), optionally in combination with salicylic acid and/or glycolic acid.

Further aspects, features and advantages of the present invention will be better appreciated upon a reading of the detailed description of the invention.

DETAILED DESCRIPTION OF THE INVENTION

Detailed embodiments of the present invention are disclosed herein; however, it is to be understood that the disclosed embodiments are merely illustrative of the invention that may be embodied in various forms. In addition, each of the examples given in connection with the various embodiments of the invention are intended to be illustrative, and not restrictive. Therefore, specific structural and functional details disclosed herein are not to be interpreted as limiting, but merely as a representative basis for teaching one skilled in the art to variously employ the present invention.

All terms used herein are intended to have their ordinary meaning unless otherwise provided. By "cosmetically acceptable," it is meant that a particular component is generally regarding as safe and non-toxic at the levels employed. The term "prevent," as used herein, includes delaying the onset of or progression of a particular sign of skin aging. The term "thin skin" includes skin that becomes thinner with chronological aging as well as prematurely thinned skin, which may be caused, for example, by photo-aging. In one embodiment, the prematurely thinned skin has been diagnosed as such by a clinician. The phrase "individual in need thereof" refers to a human that could benefit from improved dermal appearance or health, including males or females, typically females. The term "skin" includes, without limitation, the lips, skin of the face, hands, arms, neck, scalp, and chest. As used herein, the term "consisting essentially of" is intended to limit the invention to the specified materials or steps and those that do not materially affect the basic and novel characteristics of the claimed invention, as understood from a reading of this specification.

As used herein, the term "PLOD-2" refers to the enzyme procollagen-lysine, 2-oxoglutarate 5-dioxygenase 2 (lysine hydroxylase-2), in all of its various isoforms, from an organism including without limitation human, mouse, or other animal. In some embodiments, the PLOD-2 enzyme is human PLOD-2, including without limitation Isoform CRA_a (Accession No. EAW78939.1; see also Isoform 2 Precursor, Accession No. NP_891988.1), Isoform CRA_b (Accession No. EAW78940.1), and Isoform CRA_c (Accession No. EAW78941.1; see also Isoform 1 Precursor, Accession No. NP_000926.2). The nomenclature used herein to describe specific PLOD-2 examples is that of the National Center for Biotechnology Information ("NCBI"), Accession Numbers EAW78939.1 (Isoform CRA_a), NP_891988.1 (Isoform 2 Precursor), EAW78940.1 (Isoform CRA_b), EAW78941.1 (Isoform CRA_c), and NP_000926.2 (Isoform 1 Precursor), which are hereby incorporated by reference.

The cosmetic compositions of this invention comprise a combination of N-Acetyl-Tyrosinamide and a retinoid. N-Acetyl-Tyrosinamide is described in U.S. Pat. No. RE 41,278 or U.S. Pat. No. RE 41,339, the disclosures of which are hereby incorporated by reference. Cosmetically acceptable acid addition salts of N-Acetyl-Tyrosinamide are also suitable. Retinoids may be without limitation retinol (Vitamin A) and alkyl esters thereof, such as retinyl palmitate, retinyl acetate and retinyl propionate, and salts thereof, retinaldehyde, or retinoic acid (e.g., all-trans or 13-cis) and derivatives thereof. The cosmetic compositions of this invention may further comprise alpha-hydroxy acids, such as glycolic acid.

The cosmetic composition of the invention include an effective amount of N-Acetyl-Tyrosinamide and an effective amount of a retinoid of the invention, and optionally may be formulated with other cosmetically acceptable components, and vehicles, into a composition for topical application to the skin. The compositions are topically applied to the skin in effective amounts, by which is meant an amount sufficient to achieve a measurable improvement in skin health or reduction in one or more dermatological signs of aging with daily (once, twice, etc.) administration, typically for a period of at least one week or more. Such signs of skin aging include without limitation, the following:

(a) treatment, reduction, and/or prevention of fine lines or wrinkles;
(b) reduction of skin pore size;
(c) improvement in skin thickness, plumpness, and/or tautness;
(d) improvement in skin smoothness, suppleness and/or softness;
(e) improvement in skin tone, radiance, and/or clarity;
(f) improvement in procollagen, and/or collagen production;
(g) improvement in maintenance and remodeling of elastin;
(h) improvement in skin texture and/or promotion of retexturization;
(i) improvement in skin barrier repair and/or function;
(j) improvement in appearance of skin contours;
(k) restoration of skin luster and/or brightness;
(l) replenishment of essential nutrients and/or constituents in the skin;
(m) improvement of skin appearance decreased by aging and/or menopause;
(n) improvement in skin moisturization;
(o) increase in skin elasticity and/or resiliency;
(p) treatment, reduction, and/or prevention of skin sagging;
(q) improvement in skin firmness; and/or
(r) reduction of pigment spots and/or mottled skin; and
(s) improvement of optical properties of skin by light diffraction or reflection.

In practice, the compositions of the invention, including an effective amount of N-Acetyl-Tyrosinamide and an effective amount of a retinoid, alone, or in cosmetically acceptable vehicles, are applied to skin in need of treatment. That is, skin which suffers from a deficiency or loss in any of the foregoing attributes or which would otherwise benefit from improvement in any of the foregoing skin attributes. The skin is typically treated once or twice daily. The treatment may continue for a week, two weeks, four weeks, eight weeks, six months or longer.

In one embodiment the compositions are topically applied, in a cosmetically acceptable vehicle, to skin suffering from fine lines and/or wrinkles to prevent, treat, and/or ameliorate the appearance of the fine lines and/or wrinkles in the skin. In this case, the compositions are applied to skin in need of treatment, by which is meant skin already having wrinkles and/or fine lines or skin that is at risk of developing fine lines and/or wrinkles. The compositions may be applied directly to the fine lines and/or wrinkles on the skin of the face, neck, lips, chest, and/or hands. The combination of an effective amount of N-Acetyl-Tyrosinamide and an effective amount of a retinoid can remediate signs of aging by enhancing production of collagen in skin.

In one embodiment, the invention is directed to a method of improving the aesthetic appearance of skin by increasing the production of collagen in the skin, the method comprising topically applying to an area of the skin in need thereof an effective amount of N-Acetyl-Tyrosinamide and an effective amount of a retinoid (e.g., reintol or retinyl esters).

The compositions can include a cosmetically acceptable vehicle. Such vehicles may take the form of any known in the art suitable for application to skin and may include, but are not limited to, water; vegetable oils; mineral oils; esters such as octal palmitate, isopropyl myristate and isopropyl palmitate; ethers such as dicapryl ether and dimethyl isosorbide; alcohols such as ethanol and isopropanol; fatty alcohols such as cetyl alcohol, cetearyl alcohol, stearyl alcohol and biphenyl alcohol; isoparaffins such as isooctane, isododecane and is hexadecane; silicone oils such as cyclomethicone, hydrocarbon oils such as mineral oil, petrolatum, isoeicosane and polyisobutene; polyols such as propylene glycol, glycerin, butylene glycol, pentylene glycol and hexylene glycol; liposomes; waxes; or any combinations or mixtures of the foregoing.

The vehicle may comprise an aqueous phase, an oil phase, an alcohol, a silicone phase or mixtures thereof and may be in the form of an emulsion. Non-limiting examples of suitable emulsions include water-in-oil emulsions, oil-in-water emulsions, silicone-in-water emulsions, water-in-silicone emulsions, polyol-in-oil emulsions, oil-in-polyol, polyol-in-silicone, and silicone-in-polyol emulsions, wax-in-water emulsions, water-oil-water triple emulsions or the like. The emulsion may include an emulsifier (e.g., 0.01% to 10% by weight), such as a nonionic, anionic or amphoteric surfactant, or a gelling agent.

The topical composition will typically have a pH range from 1 to 8, with a pH in the range of from 2 to 7 being typical. In some embodiment, the composition will have a pH in the range of from 3.5 to 5.5. In another embodiment, the pH of the cosmetic formulation is maintainted at or below 4.0 so as to enhance retinol stability. Suitable pH adjusters such as citric acid and triethanolamine may be added to bring the pH within the desired range.

In one embodiment of the invention, the compositions may include additional skin actives, including but not limited to, retinoids, botanicals, keratolytic agents, desquamating agents, keratinocyte proliferation enhancers, collagenase inhibitors, elastase inhibitors, depigmenting agents, antiinflammatory agents, steroids, anti-acne agents, antioxidants, and advanced glycation end-product (AGE) inhibitors.

The composition may comprise additional active ingredients having anti-aging benefits, as it is contemplated that synergistic improvements may be obtained with such combinations. Exemplary anti-aging components include, without limitation, botanicals (e.g., *Butea frondosa* extract); phytol; thiodipropionic acid (TDPA) and esters thereof; retinoids (e.g., 9-cis retinoic acid, 13-cis retinoic acid, all-trans retinoic acid and derivatives thereof, phytanic acid, retinol (Vitamin A) and esters thereof, such as retinol palmitate, retinol acetate and retinol propionate, and salts thereof and others); hydroxy acids (including alpha-hydroxy acids and beta-hydroxy acids), salicylic acid and alkyl salicylates; exfoliating agents (e.g., glycolic acid, 3,6,9-trioxaundecanedioic acid, etc.), estrogen synthetase stimulating compounds (e.g., caffeine and derivatives); compounds capable of inhibiting 5 alpha-reductase activity (e.g., linolenic acid, linoleic acid, finasteride, and mixtures thereof); and barrier function enhancing agents (e.g., ceramides, glycerides, cholesterol and its esters, alpha-hydroxy and omega-hydroxy fatty acids and esters thereof, etc.), to name a few.

Exemplary retinoids include, without limitation, retinoic acid (e.g., all-trans or 13-cis), and derivatives thereof, retinaldehyde, retinol (Vitamin A) and esters thereof, such as retinol palmitate, retinol acetate and retinol propionate, and salts thereof. It is contemplated that combinations of N-Acetyl-Tyrosinamide with any of these retinoids will provide enhanced or synergistic improvements to skin. The retinoids will typically be included in amounts from about 0.0001% to about 5% by weight, or from about 0.01% to about 2.5% by weight, or from about 0.1% to about 1.0% by weight. Compositions according to this embodiment will typically include antioxidants and/or chelators such as ascorbic acid, BHT, and/or disodium EDTA, alone or in combination.

In another embodiment, the topical compositions of the present invention may also include one or more of the following: a skin penetration enhancer; an emollient, such as isopropyl myristate, petrolatum, silicones (e.g., methicone, dimethicone), oils, mineral oils, and fatty acid esters; a humectant, such as glycerin or caprylyl glycol; a skin plumper, such as palmitoyl oligopeptide, collagen, or collagen and/or glycosaminoglycan (GAG) enhancing agents; a sunscreen, such as avobenzone; an exfoliating agent; and an antioxidant.

Suitable exfoliating agents include, for example, alpha-hydroxy acids, beta-hydroxy acids, oxa-acids, oxadiacids, and their derivatives such as esters, anhydrides and salts thereof. Suitable hydroxy acids include, for example, glycolic acid, lactic acid, malic acid, tartaric acid, citric acid, 2-hydroxyalkanoic acid, mandelic acid, salicylic acid and derivatives thereof. A notable exfoliating agent is glycolic acid. When present, the exfoliating agent may comprise from about 0.01% to about 20% by weight of the composition.

Examples of antioxidants that may be used in the present compositions include compounds having phenolic hydroxy functions, such as ascorbic acid and its derivatives/esters; beta-carotene; catechins; curcumin; ferulic acid derivatives (e.g., ethyl ferulate, sodium ferulate); gallic acid derivatives (e.g., propyl gallate); lycopene; reductic acid; rosmarinic acid; tannic acid; tetrahydrocurcumin; tocopherol and its derivatives; uric acid; or any mixtures thereof. Other suitable antioxidants are those that have one or more thiol functions (—SH), in either reduced or non-reduced form, such as glutathione, lipoic acid, thioglycolic acid, and other sulfhydryl compounds. The antioxidant may be inorganic, such as bisulfites, metabisulfites, sulfites, or other inorganic salts and acids containing sulfur. In one particular embodiment, the inventive compositions will include a combination of retinol, TDPA or an ester thereof, and a N-Acetyl-Tyrosinamide. Compositions of the present invention may comprise an antioxidant (e.g., from about 0.001 wt % to about 10 wt %, or from about 0.01 wt % to about 5 wt %, of the total weight of the composition).

Other conventional additives include: vitamins, such as tocopherol and ascorbic acid; vitamin derivatives such as ascorbyl monopalmitate; thickeners such as hydroxyalkyl cellulose; gelling agents; structuring agents; metal chelating agents such as EDTA or salts thereof; pigments; colorants; and pH adjusters. The composition may optionally comprise other components known to those skilled in the art including, but not limited to, film formers, moisturizers, minerals, viscosity and/or rheology modifiers, anti-acne agents, insect repellents, skin cooling compounds, skin protectants, lubricants, fragrances, preservatives, stabilizers, and mixtures thereof. In addition to the foregoing, the cosmetic compositions of the invention may contain any other compound for the treatment of skin disorders.

The composition may be formulated in a variety of product forms, such as, for example, an emulsion, lotion, cream, serum, spray, aerosol, cake, ointment, essence, gel, paste, patch, pencil, towelette, mask, stick, foam, elixir, concentrate, and the like, particularly for topical administration. Typically, the composition is formulated as an emulsion, lotion, cream, ointment, serum or gel.

The invention provides a method for treating aging skin by topically applying a composition an effective amount of N-Acetyl-Tyrosinamide and an effective amount of a retinoid, in a cosmetically acceptable vehicle, over the affected area for a period of time sufficient to remediate, reverse, reduce, ameliorate, or prevent dermatological signs of aging.

Generally, the improvement in the condition and/or aesthetic appearance is selected from the group consisting of: reducing dermatological signs of chronological aging, photo-aging, hormonal aging, and/or actinic aging; preventing and/or reducing the appearance of lines and/or wrinkles; reducing the noticeability of facial lines and wrinkles, facial wrinkles on the cheeks, forehead, perpendicular wrinkles between the eyes, horizontal wrinkles above the eyes, and around the mouth, marionette lines, and particularly deep wrinkles or creases; improving the appearance of suborbital lines and/or periorbital lines; reducing the appearance of crow's feet; rejuvenating and/or revitalizing skin, particularly aging skin; reducing skin fragility; preventing and/or reversing of loss of glycosaminoglycans and/or collagen; ameliorating the effects of estrogen imbalance; preventing skin atrophy; preventing, reducing, and/or treating hyperpigmentation or hypopigmentation; minimizing skin discoloration; improving skin tone, radiance, clarity and/or tautness; preventing, reducing, and/or ameliorating skin sagging; improving skin firmness, plumpness, suppleness and/or softness; improving procollagen and/or collagen production; improving skin texture and/or promoting retexturization; improving skin barrier repair and/or function; improving the appearance of skin contours; restoring skin luster and/or brightness; minimizing dermatological signs of fatigue and/or stress; resisting environmental stress; replenishing ingredients in the skin decreased by aging and/or menopause; improving communication among skin cells; increasing cell proliferation and/or multiplication; increasing skin cell metabolism decreased by aging and/or menopause; retarding cellular aging; improving skin moisturization; enhancing skin thickness; slowing or halting skin thinning; increasing skin elasticity and/or resiliency; enhancing exfoliation; improving microcirculation; decreasing and/or preventing cellulite formation; and any combinations thereof.

In one embodiment, the compositions will be used to reduce the severity of wrinkles, often in combination with additional anti-aging ingredients. In another embodiment, the compositions may include an alpha-hydroxy (e.g., glycolic) or beta-hydroxy (e.g., salicylic) acid. In another embodiment, the compositions comprise N-Acetyl-Tyrosinamide (e.g., about 0.001% to about 5% w/w), a retinoid (e.g., retinol) (e.g., about 0.001 to about 5% w/w), and glycolic acid (e.g., about 0.001 to about 5% w/w). In yet another embodiment, the composition comprises N-Acetyl-Tyrosinamide (e.g., about 0.001% to about 5% w/w), a retinoid (e.g., retinol) (e.g., about 0.001 to about 5% w/w), and salicylic acid (e.g., about 0.01 to about 10% w/w).

In one embodiment, the compositions will comprise from about 0.00001% to about 90%, more typically from about 0.001% to about 25%, including from about 0.01 to about 10%, or about 0.01 to about 2.5%, or about 0.025% to about 1% by weight of N-Acetyl-Tyrosinamide. In one embodiment, the compositions will comprise from about 0.00001% to about 90%, more typically from about 0.001% to about 25%, including from about 0.01 to about 10%, or about 0.01 to about 2.5%, or about 0.025% to about 1% by weight of a retinoid (e.g., retinol).

The composition will typically be applied to the skin one, two, or three times daily for as long as is necessary to achieve desired results. The treatment regiment may comprise daily application for at least one week, at least two weeks, at least four weeks, at least eight weeks, or at least twelve weeks or more. Chronic treatment regimens are also contemplated. The effect of a composition on the formation or appearance of fine lines and wrinkles can be evaluated qualitatively, e.g., by visual inspection, or quantitatively, e.g., by microscopic or computer assisted measurements of wrinkle morphology (e.g., the number, depth, length, area, volume and/or width of wrinkles per unit area of skin). In one embodiment, the composition of the invention will be applied to the skin in an amount from about 0.001 to about 100 mg/cm$^2$, typically from about 0.01 to about 20 mg/cm$^2$, and more typically about 0.1 to about 10 mg/cm$^2$.

It is also contemplated that the compositions of the invention will be useful for treating thin skin by topically applying the composition to thin skin of an individual in need thereof. "Thin skin" is intended to include skin that is thinned due to chronological aging, menopause, or photodamage and skin that is thinning prematurely. In some embodiments, the treatment is for thin skin in men, whereas other embodiments treat thin skin in women, pre-menopausal or post-menopausal, as it is believed that skin thins differently with age in men and women, and in particular in women at different stages of life.

The method of the invention may be employed prophylactically to forestall aging including in individuals that have not manifested signs of skin aging, most commonly in individuals under 25 years of age. The method may also reverse or treat signs of aging once manifested as is common in individuals over 25 years of age, or to slow the progression of dermatological aging in such individuals.

In one embodiment, the compositions of the invention are applied to human skin to reduce sebum production or improve the appearance of skin affected by cellulite, and/or reduce unwanted lipogenesis or increase lipolysis. In this embodiment, the compounds or agents (PLOD-2 stimulators) can be formulated in cosmetically acceptable vehicles (as described herein) and may include one or more additional agents such as anti-acne ingredients (e.g., salicylic acid, benzoyl peroxide and other peroxides, sulfur, retinoids, etc.) in the case of a facial composition, or, in the case of a cellulite treatment, the formulation may comprise any ingredients suitable for treatment of cellulite, including without limitation, perilla oil and other unsaturated fatty oils and omega-3 fatty acids such as alpha-linolenic acid; caffeine; theophylline; xanthines; retinoids (e.g., retinol); and the like. A cellulite treatment according to the invention will typically be applied topically to skin suffering from cellulite, including skin of the buttocks and thighs for a period of time sufficient to improve the appearance thereof, including for example, daily treatment for at least four weeks, at least eight weeks, at least twelve weeks, or longer.

In another embodiment, the compositions of the invention are applied to human skin for depigmentation, including reducing areas of unwanted pigmentation, such as hyperpigmentation, including age spots and freckles. In this embodiment, the compositions can be formulated in cosmetically acceptable vehicles (as described herein) and may include one or more additional agents that combat pigmentation or hyperpigmentation, including tyrosinase inhibitors and/or melanosome transfer inhibitors. Special mention may be made of thiodipropionic acid and esters thereof (notably, di-lauryl esters); hydroquinone and the monobenzyl ether thereof; hydroquinone-beta-D-glucopyranoside; retinoids (e.g., retinoic acid); tretinoin; azelaic acid; Kojic acid (5-hydroxy-4-pyran-4-one-2-methyl); Mequinol (4-hydroxyanisole); Niacinamide; soy protein and other serine protease inhibitors; paper mulberry extract; Glabridin (licorice extract); *Arctostaphylos patula* and *Arctostaphylos viscida* extracts; Magnesium-L-ascorbyl-2-phosphate (MAP); 4-Isopropylcatechol; Aleosin; N-acetyl-4-S-cysteaminylphenol and N-propionyl-4-S-cysteaminylphenol; N-acetyl glucosamine; and Tranexamic acid (trans-4-aminomethylcyclohexanecarboxylic acid); to name a few.

EXAMPLES

The following examples describe specific aspects of the invention to illustrate the invention but should not be construed as limiting the invention, as the examples merely provide specific methodology useful in the understanding and practice of the invention and its various aspects.

Example 1

PLOD-2 Expression Declines with Age

Cell Treatment:
Normal Human dermal fibroblasts (donor cells from three young donors, average age 20 years, and from three older donors, average age 60 years) were grown in DMEM (Mediatech; cat. #: 15-013-CV) containing 10% Fetal Bovine Serum (Perbio; cat. #: SH30070.03), Penicillin/Streptomycin (Mediatech, Cat #30-001-C1), L-Glutamine (Mediatech; cat. #: 25-005-CI) at 37° C. and 10% $CO_2$. Cells were grown to about 80% confluence at P4/P5. RNA was isolated using RNeasy RNA extraction kit (74106) from Qiagen. RNA concentrations were determined using Nano-Drop Spectrophotometer ND 1000 (Agilent Technologies).

Reverse Transcription (RT):

Equal concentrations of RNA from three young donors (average age 20 years) and from three older donors (average age 60 years) were pooled for analysis. RT reactions were conducted in a total volume of 20 μl using High Capacity cDNA kit from AB (PN 4368814). The RT mixture was prepared to contain 2 μl 10× TaqMan RT buffer, 1.2 μl dNTP mix (100 nm), 1.0 μl 10× Random Hexamer, 1 μl RNase Inhibitor, 1 μl MultiScribe Reverse Transcriptase (50 U/ml), 100 ng of RNA, and RNase-free water to make up the final volume of 20 μl. The reaction was incubated at 25° C. for 10 min, 45° C. for 45 min, and then 95° C. for 5 min in a BIORAD MY CYCLER.

Polymerase Chain Reaction (PCR):

QPCR was carried out using Applied Biosystems Universal PCR Master Mix (PN 4369016). The mixture contained 10 μl of Taqman Universal PCR mix, 1 μl of primer and probe mix, 2 μl of RT product, and 7 μl of deionized water. All probes, Taqman assays were, were purchased from Applied Biosystems, Hs01118190_m1 for PLOD-2, and human GAPDH (PN 4352934). The temperature profiles for qPCR were 50° C. for 2 min, and 95° C. for 10 min for 1 cycle, then at 95° C. for 15 sec, and 60° C. for 1 min for 40 cycles carried out in Stratagene Mx 3005P qPCR machine.

Results:

The age related expression of PLOD-2 in younger versus older skin fibroblasts is examined. Data in Table 1 demonstrates that there is a significantly lower level of PLOD-2 in older compared to younger skin fibroblasts. All values are statistically significant at $p<0.05$.

TABLE 1

| Age | Relative PLOD-2 Level |
|---|---|
| Young | 100% |
| Old | 27% |

PLOD-2 gene expression significantly declines with age in normal human dermal fibroblasts, in vitro. Since PLOD-2 modification is critical for the stability of procollagen, a decline in PLOD-2 expression can lead to a decrease in collagen production; thereby resulting in less support in the dermal matrix and contributing to wrinkle formation.

Example 2

PLOD-2 Levels Modulate Collagen Production

Cell Treatment:

Young normal Human dermal fibroblasts (~22 yrs) were grown in DMEM (Mediatech; cat. #: 15-013-CV) containing 10% Fetal Bovine Serum (Perbio; cat. #: SH30070.03), Penicillin/Streptomycin (Mediatech, Cat #30-001-C1), L-Glutamine (Mediatech; cat. #: 25-005-CI) at 37° C. and 10% $CO_2$. Small interference RNA (siRNA) On-TARGETplus siRNA against PLOD-2 (Sequences: ACAUCAUGAUAGCCGUAUA; AAAUCUAAGUCAAGCGGAA; ACACAACCGAGGAGCGUAU; CGGAGAAGCCCUCGAGCAU) (Dharmacon Inc, Human, L-004285-01-0005) or siCONTROL nontargeting/scrambled siRNA (Dharmacon D001810-10-05) were transfected into cells at a final concentration of 50 nM using Lipofectamine (Invitrogen, 12252-011) following manufacturer's protocol. 72 hrs post-transfection RNA was isolated using RNeasy RNA extraction kit (74106) from Qiagen. RNA concentrations were determined using NanoDrop Spectrophotometer ND 1000 (Agilent Technologies). Conditioned Tissue culture medium was collected for procollagen analysis.

Reverse Transcription (RT):

RT reactions were conducted in a total volume of 20 μl using High Capacity cDNA kit from AB (PN 4368814). The RT mixture was prepared to contain 2 μl 10× TaqMan RT buffer, 1.2 μl dNTP mix (100 nm), 1.0 μl 10× Random Hexamer, 1 μl RNase Inhibitor, 1 μl MultiScribe Reverse Transcriptase (50 U/ml), 100 ng of RNA, and RNase-free water to make up the final volume of 20 μl. The reaction was incubated at 25° C. for 10 min, 45° C. for 45 min, and then 95° C. for 5 min in a BIORAD MY CYCLER.

Polymerase Chain Reaction (PCR):

QPCR was carried out using Applied Biosystems Universal PCR Master Mix (PN 4369016). The mixture contained 10 μl of Taqman Universal PCR mix, 1 μl of primer and probe mix, 2 μl of RT product, and 7 μl of deionized water. All probes, Taqman assays were, were purchased from Applied Biosystems, Hs01118190_m1 for PLOD-2, and human GAPDH (PN 4352934). The temperature profiles for qPCR were 50° C. for 2 min, and 95° C. for 10 min for 1 cycle, then at 95° C. for 15 sec, and 60° C. for 1 min for 40 cycles carried out in Stratagene Mx 3005P qPCR machine.

Procollagen Assay:

Procollagen levels in the conditioned medium were determined using ProcollagenType-1 C-Peptide EIA Kit from Takara; cat. #MK101 as per manufacturer's suggestions. Reading was measured at 450 nm using a spectrophotometer.

Results:

Human dermal fibroblasts (age—22 yrs) treated with siRNA against PLOD-2 for 72 hrs showed a signification decrease in PLOD-2 mRNA compared to cells treated with control siRNA. In addition, the conditioned medium from samples treated with siRNA against PLOD-2 demonstrated a significant decrease in procollagen levels, relative to control treated cells, as shown in Table 2. These data indicate that suppression of PLOD-2 leads to a decrease in the level of procollagen production. All values are statistically significant at $p<0.05$.

TABLE 2

| Treatment | Relative PLOD-2 Expression | Relative Procollagen Level |
|---|---|---|
| Control (Scrambled siRNA 50 nM) | 100% | 100% |
| PLOD-2 siRNA 50 nM | 20% | 85% |

Example 3

PLOD-2 Enzyme Stimulation Assay

Cell Treatment:

Normal Human dermal fibroblasts were grown in DMEM (Mediatech; cat. #: 15-013-CV) containing 10% Fetal Bovine Serum (Perbio; cat. #: SH30070.03), Penicillin/Streptomycin (Mediatech, Cat #30-001-C1), L-Glutamine (Mediatech; cat. #: 25-005-CI) at 37° C. and 10% $CO_2$. Cells were stripped of serum overnight, followed by treatment with 0.05% N-Acetyl-Tyrosinamide or vehicle (DMSO), in the absence of serum for 48 hours. RNA was isolated using RNeasy RNA extraction kit (74106) from Qiagen. RNA concentrations were determined using NanoDrop Spectrophotometer ND 1000 (Agilent Technologies).

Reverse Transcription (RT):

RT reactions were conducted in a total volume of 20 μl using the High Capacity cDNA kit from AB (PN 4368814). The RT mixture was prepared to contain 2 μl 10× TaqMan RT buffer, 1.2 μl dNTP mix (100 nm), 1.0 μl 10× Random Hexamer, 1 μl RNase Inhibitor, 1 μl MultiScribe Reverse Transcriptase (50 U/ml), 100 ng of RNA, and RNase-free water to make up the final volume of 20 μl. The reaction was incubated at 25° C. for 10 min, 45° C. for 45 min, and then 95° C. for 5 min in a BIORAD MY CYCLER.

Polymerase Chain Reaction (PCR):

QPCR was carried out using Applied Biosystems Universal PCR Master Mix (PN 4369016). The mixture contained 10 μl of Taqman Universal PCR mix, 1 μl of primer and probe mix, 2 μl of RT product, and 7 μl of deionized water. All probes, Taqman assays were, were purchased from Applied Biosystems, Hs01118190_m1 for PLOD-2, and human GAPDH (PN 4352934). The temperature profiles for qPCR were 50° C. for 2 min, and 95° C. for 10 min for 1 cycle, then at 95° C. for 15 sec, and 60° C. for 1 min for 40 cycles carried out in Stratagene Mx 3005P qPCR machine.

Results:

Cells treated with a solution containing 0.05% N-Acetyl-Tyrosinamide demonstrated a significant increase in PLOD-2 levels, relative to control, vehicle treated cells, as shown by the data in Table 3. Data represents an average of two or three independent experiments. All values are statistically significant at $p<0.05$.

TABLE 3

| Treatment | Relative PLOD-2 Expression |
| --- | --- |
| Vehicle (DMSO) | 100% |
| N-Acetyl-Tyrosinamide (0.05%) | 180% |

These results show that N-Acetyl-Tyrosinamide stimulates the expression of PLOD-2 in normal Human Dermal Fibroblasts, in vitro. Because PLOD-2 modification is critical for the stability of procollagen, a key building block of the dermis, a decline in PLOD-2 expression can lead to a decrease in collagen production, thereby resulting in the weakening of the dermal matrix and therefore contribute to wrinkle formation. The data in Table 3, shows that N-Acetyl-Tyrosinamide can help to intercept critical collagen blockers to increase skin's key building blocks and thus generate new collagen to help fill wrinkles Example 4

Stimulation of Collagen, Fibrillin and Elastin Production

Cell Treatment:

Normal Human dermal fibroblasts were grown in DMEM (Mediatech; cat. #: 15-013-CV) containing 10% Fetal Bovine Serum (Perbio; cat. #: SH30070.03), Penicillin/Streptomycin (Mediatech, Cat #30-001-C1), L-Glutamine (Mediatech; cat. #: 25-005-CI) at 37° C. and 10% $CO_2$. Cells were stripped of serum overnight, followed by treatment with a solution containing 0.05% N-Acetyl-Tyrosinamide or vehicle (DMSO), in the absence of serum for 48 hours. RNA was isolated using RNeasy RNA extraction kit (74106) from Qiagen. RNA concentrations were determined using Nano-Drop Spectrophotometer ND 1000 (Agilent Technologies).

Reverse Transcription (RT):

RT reactions were conducted in a total volume of 20 μl using High Capacity cDNA kit from AB (PN 4368814). The RT mixture was prepared to contain 2 μl 10× TaqMan RT buffer, 1.2 μl dNTP mix (100 nm), 1.0 μl 10× Random Hexamer, 1 μl RNase Inhibitor, 1 μl MultiScribe Reverse Transcriptase (50 U/ml), 100 ng of RNA, and RNase-free water to make up the final volume of 20 μl. The reaction was incubated at 25° C. for 10 min, 45° C. for 45 min, and then 95° C. for 5 min in a BIORAD MY CYCLER.

Polymerase Chain Reaction (PCR):

QPCR was carried out using Applied Biosystems Universal PCR Master Mix (PN 4369016). The mixture contained 10 μl of Taqman Universal PCR mix, 1 μl of primer and probe mix, 2 μl of RT product, and 7 μl of deionized water. All probes, Taqman assays were, were purchased from Applied Biosystems, COL1a-Hs00164004_ml, ELN-Hs00355783_m1, FBN1-Hs00171191_m1, and human GAPDH (PN 4352934). The temperature profiles for qPCR were 50° C. for 2 min, and 95° C. for 10 min for 1 cycle, then at 95° C. for 15 sec, and 60° C. for 1 min for 40 cycles carried out in Stratagene Mx 3005P qPCR machine.

Results:

Human dermal fibroblasts treated with 0.05% N-Acetyl-Tyrosinamide for 48 hours was analyzed by qRT-PCR for expression levels of COL1a, ELN and FBN1, using GAPDH as an internal control. Cells treated with N-Acetyl-Tyrosinamide demonstrated a significant increase in COL1a, relative to control, vehicle treated cells. In addition, cells treated with N-Acetyl-Tyrosinamide also showed a significant increase in ELN and FBN1 as shown in Table 4. All values are statistically significant at $p<0.05$.

TABLE 4

| | Pro-collagen | Elastin | Fibrillin |
| --- | --- | --- | --- |
| N-Acetyl-Tyrosinamide (0.05%) | 16% | 29% | 29% |

Collagen, Elastin and Fibrillin are key building blocks of the dermis, decline with age, and thus contribute to wrinkle formation. The data in Table 4 shows that N-Acetyl-Tyrosinamide helps increase pro-collagen, which will generate new collagen to help fill wrinkles Example 5

An Exemplary N-acetyl Tyrosidamide/Retinoid Composition

An exemplary cosmetic composition representing an embodiment of the instant invention is reprinted below. In one embodiment, the concentration of n-acetyltyrosidamide ranges between about 0 and about 2 percent. In another embodiment, the concentration of n-acetyltyrosidamide ranges between about 0.05 and about 1 percent. In one embodiment, the concentration of retinol ranges from between about 0.05 to about 0.5%. In another embodiment, the concentration of retinol ranges from between about 0.1% to about 0.3%. In another embodiment, the concentration of retinol ranges from between about 0.15% to about 0.25%.

Water
Glycerin
Ethylhexyl Isononanoate
Octyldodecanol
Dimethicone
Butylene Glycol Polymethyl methacrylate
Trisiloxane
Hydroxyl acrylate/sodium acryloyldimethyltaurate copolymer
Isohexadecane
N-acetyl tyrosidamide
Dimethiconol
PEG-100 Stearate
Laureth-4
Polysorbate 60
Polysorbate 20
Ascorbic acid
BHT
Sodium hydroxide
Disodium EDTA
Retinol
Phenoxyethanol
Methylparaben All references including patent applications and publications cited herein are incorporated herein by reference in their entirety and for all purposes to the same extent as if each individual publication or patent or patent application was specifically and individually indicated to be incorporated by reference in its entirety for all purposes. Many modifications and variations of this invention can be made without departing from its spirit and scope, as will be apparent to those skilled in the art. The specific embodiments described herein are offered by way of example only, and the invention is to be limited only by the terms of the appended claims, along with the full scope of equivalents to which such claims are entitled.

The invention claimed is:

1. A method for treatment of fine lines and/or wrinkles in human skin comprising topically applying to an area of the skin in need thereof a composition comprising:
   an effective amount of N-Acetyl-Tyrosinamide and
   an effective amount of a retinoid,
for a time sufficient to reduce the severity of said fine lines and/or wrinkles.

2. The method according to claim 1, wherein said composition is applied to said skin at least once daily for a period of at least four weeks.

3. The method according to claim 1, further comprising topically applying to said area of the skin in need thereof an effective amount of glycolic acid.

4. The method according to claim 1, further comprising topically applying to said area of the skin in need thereof an effective amount of salicylic acid.

5. The method according to claim 1, wherein said composition further comprises:
   water,
   glycerin,
   ethylhexyl isononanoate,
   octyldodecanol,
   dimethicone,
   butylene glycol,
   polymethyl methacrylate,
   trisiloxane,
   hydroxyethyl acrylate/sodium acryloyldimethyl taurate copolymer,
   isohexadecane,
   ascorbic acid,
   BHT,
   PEG-100 Stearate,
   Laureth-4,
   Polysorbate-60,
   Dimethiconol,
   Polysorbate-20,
   Sodium hydroxide,
   Disodium EDTA,
   a preservative, and
   optionally, a fragrance.

* * * * *